United States Patent [19]

Matsunaga et al.

[11] 4,369,037
[45] Jan. 18, 1983

[54] HAIR TREATMENT COSMETICS CONTAINING CATIONIC KERATIN DERIVATIVES

[75] Inventors: Kinjiro Matsunaga, Miyashiro; Takeo Okumura, Sakura; Rikio Tsushima, Wakayama, all of Japan

[73] Assignee: Kao Soap Co., Ltd., Tokyo, Japan

[21] Appl. No.: 318,419

[22] Filed: Nov. 5, 1981

[30] Foreign Application Priority Data

Nov. 19, 1980 [JP] Japan ................. 55-162900
Nov. 20, 1980 [JP] Japan ................. 55-163784

[51] Int. Cl.³ ............................. C07G 7/00; C08H 1/06
[52] U.S. Cl. ................................ 8/127.51; 8/401; 8/405; 8/433; 260/123.7; 424/47; 424/70; 424/71; 424/72
[58] Field of Search ............ 260/123.7; 424/70, 71, 424/72, 47; 8/127.51, 401, 405, 433

[56] References Cited

U.S. PATENT DOCUMENTS

| | | | |
|---|---|---|---|
| 2,131,145 | 9/1938 | Schlack | 260/123.7 X |
| 2,398,317 | 4/1946 | Mackenzie et al. | 260/123.7 UX |
| 2,447,860 | 8/1948 | Jones et al. | 260/123.7 X |
| 2,517,572 | 8/1950 | Jones et al. | 260/123.7 X |
| 3,567,363 | 3/1971 | Wolfram | 260/123.7 UX |
| 3,634,022 | 1/1972 | Robbins et al. | 8/127.51 |
| 3,694,258 | 9/1972 | Vanderberg et al. | 260/123.7 UX |
| 3,824,228 | 7/1974 | Eckert et al. | 260/123.7 X |
| 3,842,848 | 10/1974 | Karjala | 424/71 X |
| 3,904,748 | 9/1975 | Eckert et al. | 424/71 X |
| 4,041,150 | 8/1977 | Karjala | 424/71 |
| 4,076,800 | 2/1978 | Marsh et al. | 424/70 |
| 4,195,077 | 3/1980 | Marsh et al. | 424/70 |
| 4,279,996 | 7/1981 | Yoshioka et al. | 424/70 X |

*Primary Examiner*—Howard E. Schain
*Attorney, Agent, or Firm*—Oblon, Fisher, Spivak, McClelland & Maier

[57] ABSTRACT

Cationic keratin derivatives which are obtained by reacting a part or whole of functional groups of keratin with a cationizing agent which contains in the molecule thereof a specific type of a group or groups and a quaternary nitrogen atom. The process for preparing such derivatives and a variety of cosmetics containing the same are also described.

8 Claims, No Drawings

HAIR TREATMENT COSMETICS CONTAINING CATIONIC KERATIN DERIVATIVES

BACKGROUND OF THE INVENTION

1. Field of the Invention

The present invention relates to a cationic keratin derivative, a process of its preparation and hair treating cosmetics containing it.

2. Description of the Prior Art

Hair is one of the most important portions for beauty care, and various beauty treatments are applied thereto, in which a variety of hair treating cosmetics are used. In this specification, the term "hair treating cosmetics" is used to generally represent all cosmetics applied to hair, including, for example, shampoos, hair rinsing compositions, pre-shampoo conditioners, after-shampoo conditioners, setting lotions, blow-styling lotions, hair sprays, hair dyes, bleaches, permanent wave primary agents, permanent wave oxidizing agents, hair coloring agents, and hair dressing agents such as hair liquids or hair tonics.

Conventional hair treating cosmetics are not completely satisfactory for one reason or another.

For instance, shampoos are intended to remove dirt deposited on hair, or dirt comprising decomposition products or oxides of the sebum secreted from a head skin, and their basic materials are anionic surfactants, nonionic surfactants or amphoteric surfactants. When hair is washed with shampoos containing these materials, the sebum or other oil components on the surface thereof can be excessively washed off, and the texture of hair after the washing tends to be bad, and it becomes difficult to comb or brush the hair. Further, when dried completely, the hairs tend to be hard to style. Especially in winter when humidity is low, brushing is likely to cause static electricity, which in turn causes fly-away. Hairs will thereby be tangled with one another, and become harder to comb, leading to split-ends and broken hairs.

In order to eliminate such drawbacks, it is known to incorporate oils or the like to usual shampoos so that an oil is supplemented at the time of washing hair. Various oil agents are incorporated in usual shampoos.

However, in a shampoo composition system, the entire system is maintained in an emulsified or dissolved state by a surfactant, and it has been difficult to incorporate an oil in an adequate amount for scale and hair without impairing the stability of the system.

If a substantial amount of an oil agent is incorporated, the amount of the oil adsorbed on the hair increases. However, there used to be drawbacks that the essential functions of the shampoo, such as foaming property and detergency were thereby considerably degraded, or a commercial value of the shampoo was thereby impaired.

On the other hand, there have recently proposed various shampoo compositions containing cationic polymers for the purposes of imparting a rinsing effect to the hair after washing. However, these compositions had drawbacks that (1) although they were effective for conditioning, they were inferior in foaming property and detergency, (2) they tended to be colored or underwent color change with time, (3) although they were superior in the foaming property, they were inferior in the conditioning effect, or (4) they were costly.

A hair rinse composition is designed to be used for the purposes of preventing a loss of flexibility, luster, and combing easiness of hair and a tendency for damage, split-ends or broken hairs, and providing hair conditioning effects, i.e. imparting flexibility, softness and smoothness to hair and improving combing easiness. It is composed of a quaternary ammonium salt as a cationic surfactant, and an oil component such as a liquid paraffin or a higher alcohol.

However, the quaternary ammonium salt does not have sufficient ability to emulsify or disperse an adequately effective amount of oil component in a stabilized condition, and the system was unstable. If a nonionic surfactant was incorporated to overcome the difficulty, the essential rinsing effect was degraded. Under the circumstances, there has been proposed to incorporate, instead of the above mentioned oil components, other compounds such as an anionic surfactant, an anionic polymer compound, a cationic polymer compound, or a hydrolyzed product of collagen, to obtain a stable hair rinsing composition. However, no satisfactory result has not yet been obtained.

Hair setting compositions such as a setting lotion or a hair spray, are used for the purposes of preventing loosening of set hair due to a high humidity or wind. Conventional hair setting compositions contain a resin component such as an acrylate-methacrylate co-polymer or a polyvinylpyrrolidone-vinylacetate co-polymer as a fixing agent to provide a setting effectiveness.

However, such a resin component has a poor washability, and is hardly removable completely from hair even when the hair is washed with a shampoo. Accordingly, it is likely to remain on the surface of the hair and causes undesirable phenomena such as an increase of the frictional coefficient of the hair, formation of split ends or broken hairs by brushing, and deterioration of the texture of the hair.

In order to eliminate such drawbacks, there has been an attempt to incorporate a nonionic surfactant, a wetting agent, etc. into the resin component thereby to increase the water solubility. However, this method has a drawback that the setting power under a high humidity condition will thereby be degraded and the essential property of the hair setting composition is thus lost, although the washability is thereby improved.

Pre-shampoo conditioners are designed to be applied prior to hair washing, followed by normal hair washing, and to prevent damages of the hair at the time of the washing, the rinsing, or the finishing of the hair e.g. by drying the hair with a drier and thus to impart the conditioning effects to the hair. Presently, pre-shampoo conditioners containing fats and oils such as lanolin as the major component are commercially available and favourably used. However, when hair is subjected to protecting treatment with a pre-shampoo treatment of a type containing fats and oils as the major component, the finished hair tends to be greasy and often gives rise to a drawback that the hair becomes sticky, and a further study for improvements is desired.

Permanent wave waving lotion and neutralizer are designed to set the waves of hair by reducing followed by oxidizing the hair and to be used for a permanent wave method. The permanent wave waving lotion comprise a reducing agent such as thioglycollic acid or cystein to reduce the disulfide bond (—S—S—) in the hair into hydroxysulfide an alkaline substance as the major components. Whereas, the permanent wave neutralizer comprise an oxidizing agent such as a bromate, a perborate or an aqueous hydrogen peroxide solution to oxdize S—H into disulfide bonds as the major component.

However, according to such a permanent wave method using the permanent wave waving lotion and neutralizer, the hair is subjected to severe conditions such as oxidation and reduction, and undesirable phenomena such as a decrease of the strength of the hair and a degradation of the texture of the hair occur. Such hair can hardly be combed and is likely to be hitched and damaged by peeling off of the cuticle of the hair, splitting or breakage.

The degradation of the hair by the permanent wave waving lotion is caused by the breakage of keratin constituting the hair, by the action of the permanent wave waving lotion, and consequential dissolution of proteins or amino acids. Accordingly, in order to prevent the degradation, it is necessary to supplement the thus lost protein components.

Therefore, there has hitherto been an attempt to incorporate into the waving lotion a hydrolyzed product of collagen. However, such a hydrolyzed product is likely to easily be washed off by the rinsing or washing of the hair after the cold wave treatment, and therefore, no adequate effect was obtainable.

On the other hand, the degradation of the hair by the permanent wave neutralizer is caused by the swelling of the hair by the permanent wave waving lotion, followed by the action of the neutralizer to damage the hair. In order to prevent such damages, it has been proposed to incorporate an oil agent or a wetting agent. However, none has yet been proved to be satisfactory.

Hair dyes, bleaches and hair coloring agents are intended to be used for the purpose of dyeing white hair with a black color, making up or harmonizing the hair color with the clothes. They are generally classified into those wherein oxidation colors are used, those wherein decolorizing agents are used, those wherein the dyeing is carried out by solvent assistants with use of oxidation colors, those wherein hair coloring agents are used, and those wherein iron-pyrogallol is used.

Among these, the oxidation hair dye agents are designed to have an oxidation dye intermediate of a low molecular weight penetrated into the hair and have it oxidation-polymerized within the hair to form a color for hair coloring. The bleaches are designed to oxidatively decompose melamine by an alkaline hydrogen peroxide, thereby to decolorizing and dyeing the hair. However, these coloring agents bring about chemical changes of the hair and thus, the hair is heavily damaged. Further, in the case of hair dye agents wherein oxidation colors or pigments are used (i.e. temporary hair dyes), a coloring agent merely deposits on the hair and it is likely to be removed by e.g. washing the hair. Therefore, it is necessary to repeatedly carry out the hair dyeing treatment at certain intervals. However, in doing so, the hair dyes are accumulated on the hair and tend to give damages to the surface of the hair. Furthermore, it is common to incorporate a polymer resin as a binder into a hair dye, and if such a resin remains on the hair, the hair becomes to be hardly combed or brushed and is likely to be damaged by the combing or brushing.

In order to prevent such damages to the hair, it is common to incorporate an oil agent or a wetting agent into the hair dyes. However, the effectiveness is merely temporary and inadequate, and a further improvement is desired.

On the other hand, keratin which is a fibrous protein distributed over the outer skin of a higher animal and having a function of protecting a living body, is composed of 18 different kinds of amino acids (i.e. alanine, alginine, aspartic acid, cystine, glutamic acid, glycine, histidine, isoleucine, leucine, lysine, methionine, phenylalanine, proline, serine, threonine, tryptophane, tyrosine, and valine), has a high cystine content and is characterized by a cross-linked structure having one disulfide bond (—S—S) per an average of from 10 to 20 amino acid residues.

Keratin is widely distributed in hair, nails, wools, feathers, horns, etc. Especially, it constitutes the major components of hair and nails, and is therefore believed to have good affinity to hair and skin. Accordingly, a study has been made on the incorporation of such keratin into cosmetics. However, keratin per se is insoluble in a usual solvent, and practically, the range of its application is very much limited.

In order to use keratin for e.g. cosmetics, it is firstly necessary to dissolve it in a certain solvent, e.g. in water. To do this, it is necessary to split the cross-linked disulfide bond. The splitting may be done either by reduction or by oxidation. By the reduction, the disulfide bond is converted to a sulfhydryl group (—SH) and the reduction product is called keratin. On the other hand, by the oxidation, the disulfide bond is converted to a sulfonic acid group (—SO$_3$H), and the oxidation product is called keratose. The straight chain proteins thereby obtained should essentially be water soluble. However, due to the hydrogen bond, ion bond, hydrophobic bond, etc. between the proteins themselves, they are hardly soluble in water or in an organic solvent, and, if dissolved, they give only a very dilute solution.

SUMMARY OF THE INVENTION

It is, accordingly, an object of the present invention to provide cationic keratin derivatives which are miscible with or soluble in water or aqueous systems and are thus suitably applicable to hair treating cosmetics.

It is another object of the invention to provide cationic keratin derivatives which comprise a specific type of a group and quaternary nitrogen incorporated by a specific method, whereby the derivatives are rendered soluble in water or other solvents.

It is a further object of the invention to provide a variety of hair treating cosmetic which comprise a predetermined amount of the cationic keratin derivatives of the just-mentioned type.

It is a still further object of the invention to provide a process for preparing the cationic keratin derivatives.

In accordance with one aspects of the present invention, there is provided a cationic keratin derivative which is obtained by reacting a part or whole of functional groups of keratin with a cationizing agent which contains in its molecule a group or groups represented by the formula

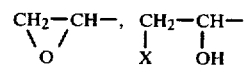

or CH$_2$=CH—
where X represents a halogen atom, and a quaternary nitrogen atom.

The resulting cationic keratin derivatives have been found to be readily soluble in water or aqueous media or mixtures of water and hydrophilic organic solvents soluble with water. These derivatives are also found that they show good affinity for hair and skin and are thus suitable as an ingredient of cosmetics.

Accordingly, according to another aspect of the invention, there is provided a hair treating cosmetic which comprises a cationic keratin derivative obtained by reacting a part or whole of functional groups of keratin with a cationizing agent which contains in its molecule both a group or groups represents by the formula

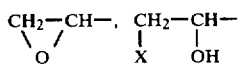

or $CH_2=CH-$
where X represents a halogen atom and a quaternary nitrogen atom. Preferably, the amount of the derivative is in the range of 0.01 to 10% by weight of the total cosmetic composition which may more or less vary depending on the type of cosmetic.

According to a further aspect of the invention, the cationic keratin derivative can be obtained by a process which comprises reducing a keratin material in water or a mixture of water and a hydrophilic organic solvent with a reducing agent to cleave disulfide bonds in the keratin material into sulfhydryl groups, and reacting a cationizing agent with the reduction product, the cationizing agent containing in its molecule both a group or groups of the following formulas

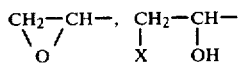

and $CH_2=CH-$
wherein X has the same meaning as defined above and a quaternary nitrogen atom.

DETAILED DESCRIPTION AND EMBODIMENTS OF THE INVENTION

As the keratin material, i.e. a starting material to obtain keratin, there may be mentioned animal hairs, human hairs, feathers, nails, horns, hoofs, scales, and the like. Wools, feathers and human hairs are particularly preferred. These keratin substances may be subjected to reduction treatment as they are, or prior to such treatment, they may be subjected to hydrolysis treatment. The keratin substances may further be pretreated, as the case requires, by pulverizing or cutting into suitable sizes, by washing, by defatting, or by heating at a high temperature, followed by abrupt discharge into the atmosphere for puffing.

The hydrolysis treatment may be conducted by either an acid, an alkali or an enzyme. There is no particular limitation as to the conditions for the hydrolysis. However, it is preferred that the hydrolyzed products have a molecular weight of from 500 to 10,000, more preferably from 1,000 to 5,000. Those having a molecular weight less than 500 are less effective, but they are still useful if used in a great amount, although they have a drawback that their use is rather difficult. Among the above mentioned hydrolysis methods, the method wherein an enzyme is used, is especially preferred since the decomposition products have a uniform molecular weight distribution with a narrow range and the formation of free amino acids is minimal.

The reduction treatment of the keratin substances (which include the hydrolyzed products) may be carried out, for instance, by treating them with a reducing agent in water or in a mixed solvent of water and a hydrophilic organic solvent, whereby the disulfide bond (—S—S—) in the keratin substances are split into sulfhydryl groups (—SH) to give keratin. As the reducing agent, there may be used any reducing agent capable of splitting the disulfide groups in the keratin materials into the sulfhydryl groups. As such a reducing agent, there may be mentioned an alcohol such as 2-mercapto ethanol or thioglycollic acid, a thiol derivative of a carboxylic acid, a phosphorus compound such as tri-n-butylphosphine, or triphenylphosphine, an organic reducing agent such as ascorbic acid, and an inorganic reducing agent such as sodium hydrogen sulfite or sodium sulfite.

As the hydrophilic organic solvent, there may be mentioned, for instance, methanol, ethanol, n-propanol, isopropanol, acetone, methylethyl ketone, dioxane, tetrahydrofuran, dimenthylformamide, dimethyl sulfoxide, or hexamethylphosphoric triamide. There is no strict limitation as to the amount of the reaction solvent, and it is only required that the amount is sufficient to carry out the reduction reaction uniformly. Normally, the solvent is used in an amount of from 10 to 100 times the weight of the keratin material. The amount of the reducing agent to be used, is usually from 2 to 10 times, in equivalent, to the disulfide bond in the keratin substance, as the starting material. The pH of the reaction system is usually within a range of from 2 to 12, preferably within a range of from 6 to 11.

Further, the reaction temperature may usually be at rool temperature, but it is possible to shorten the reduction time by heating, as the case requires. As to the reaction time, it is required that the time is sufficient to adequately complete the reduction reaction, and it is usually from 2 to 3 hours or longer depending upon e.g. the reaction temperature. Further, the reduction reaction is preferably carried out in an inert gas atmosphere such as nitrogen. Because the sulfhydryl groups formed by the reduction reaction are very much susceptible to oxidation and they are unstable even against oxygen in the atmosphere.

The keratin thus obtained is treated with the above mentioned quarternary ammonium type cationic agent, whereby the cationizing agent is attached, to the sulfhydryl groups, or the sulfhydryl groups and other groups such as hydroxyl groups, amino groups or carboxyl groups.

The quarternary ammonium type cationizing agents which may be used in the process of the present invention, include glycidyltrimethyl ammonium chloride, glycidyltriethyl ammonium chloride, 3-chloro-2-hydroxypropyltrimethyl ammonium chloride, allyltrimethyl ammonium chloride and the corresponding bromides and iodides. Most commonly used is glycidyltrimethyl ammonium chloride.

The addition reaction of the reduction decomposition products of keratin substances and the cationizing agent is carried out by adding a cationizing agent to the reaction mixture obtained by the above mentioned reduction treatment. The cationizing agent induces the addition reaction primarily to the sulfhydryl groups of the functional groups of the reduction decomposition products. However, in case the cationizing agent is added in an amount in excess of the equivalent of the sulfhydryl groups, the addition reaction is induced also to the functional groups other than the sulfhydryl groups, such as hydroxyl groups, amino groups or carboxyl groups.

The amount of the cationizing agent is generally in the range from 0.1 to 6 times, preferably from 0.5 to 2 times, in equivalent, to the sulfhydryl groups present in the reduction decomposition products of the keratin substance. If the amount is less than 0.1 time, in equivalent, a product having adequate solubility in water and in a mixed solvent of water and a hydrophilic organic solvent can not be obtained. On the other hand, if the amount is more than 6 times, in equivalent, the essential properties of the keratin substance will be lost and such is undesirable. The reaction temperature is selected within a range of from room temperature to 90° C. However, the higher the temperature is, the more the addition reaction is facilitated. With respect to the pH of the addition reaction system, there is no necessity of pH control after the reduction reaction. Namely, the addition reaction may be carried out within a pH range of from 2 to 12, normally from 6 to 11. As the addition reaction of the quarternary ammonium salt type cationizing agent to the reduction products of keratin, proceeds, the reduction products dissolve in the reaction solvent, and finally, the insoluble components will be less than 30% of the reduction products of keratin. The insoluble components are removed by filtration, centrifugation, etc., and the solvent is distilled off partially to obtain a solution of a cationic keratin.

The solution of the cationic keratin thus obtained, is subjected to ultrafiltration or dialysis to remove low molecular weight impurities such as the reducing agent, and thereafter, it may be used as it is, or it may be subjected to freeze drying to obtain the cationic keratin in a form of a solid which is more convenient for use, storage and transportation.

As the representative cationic keratin of the present invention, there may be mentioned a cationic keratin in which a part or whole of the sulfhydryl groups of keratin is modified with a cationic group represented by the following formula,

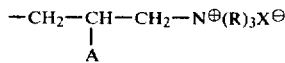

where the three R may be the same or different and represent a lower alkyl group or an aryl group, X represents a halogen atom, and A represents a hydrogen atom or a hydroxyl group. As a specific example, there may be mentioned, for instance, S-($\beta$-hydroxy-$\gamma$-trimethyl ammoniopropyl) keratin and S-($\gamma$-trimethyl ammoniopropyl) keratin.

Hair treating cosmetics of the present invention are prepared in the following manner:

(1) Shampoos:

A shampoo is prepared in a usual manner with use of the known shampoo ingredients and one or more of anionic surfactants and the cationic keratin are incorporated in the composition as essential components.

Among anionic surfactants as the basic material for the shampoo, the following surfactants are preferred:

(1) A straight chained or branched alkylbenzenesulfonate having an alkyl group of from 10 to 16 carbon atoms on an average.

(2) A polyoxyalkylenealkyl sulfuric←ester having a straight chained or branched alkyl group of from 8 to 20 carbon atoms on an average and with addition of from 0.5 to 8 moles, on an average, of ethylene oxide and/or propylene oxide in its molecule.

(3) An alkyl sulfuric←ester having an alkyl group of from 10 to 20 carbon atoms on an average.

(4) An olefin sulfonate having from 10 to 20 carbon atoms on an average in its molecule.

(5) An alkane sulfonate having from 10 to 20 carbon atoms on an average in its molecule.

(6) An alkylethoxy carboxylic ester having an alkyl group of from 10 to 20 carbon atoms on an average and with addition of from 0.5 to 8 moles, on an average, of ethylene oxide in its molecule.

(7) A succinic acid derivative represented by the formula,

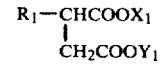

where R is an alkyl or alkenyl group having from 6 to 20 carbon atoms, and each of $X_1$ and $Y_1$ represents an ion.

As the counter ions to these anionic surfactants, there may be mentioned an alkali metal ion such as sodium, or potassium; an alkaline earth metal ion such as calcium, or magnesium; and ammonium ion and an alkanolamine having from 1 to 3 alkanol groups of from 2 or 3 carbon atoms (for instance, monoethanolamine, diethanolamine, triethanolamine or triisopropanolamine).

Among the above mentioned anionic surfactants, especially preferred are a straight chained or branched alkyl sulfate having from 10 to 16 carbon atoms on an average, a polyoxyethylene alkyl sulfate having an alkyl group of from 8 to 20 carbon atoms on an average (from 0.5 to 8 average addition moles), and an olefin sulfonate having from 10 to 16 carbon atoms on an average.

In the shampoo of the present invention, the amount of the anionic surfactant is from 5 to 30% by weight (hereinafter represented simply by %), preferably from 10 to 25%, and the amount of the cationic keratin is from 0.01 to 10%, preferably from 0.5 to 3%. If the amount of the cationic keratin is less than 0.01%, no adequate effectiveness is obtainable. On the other hand, if the amount exceeds 10%, there will be a disadvantage that the hair becomes sticky under high humidity. Thus, either case is undesirable.

As other components to be incorporated in the shampoo of the present invention, there may be mentioned an amphoteric surfactant, a nonionic surfactant, a cationic surfactant, and a solubilizing agent such as propylene glycol, glycerine, urea or the like; a viscosity controlling agent such as ethyl alcohol, isopropyl alcohol, hydroxyethylcellulose, methylcellulose, a higher alcohol or the like; a perfume, a pigment, an ultraviolet ray absorbing agent, an anti-oxidant, an anticeptic, a pearling agent a lotion-forming agent and the like. They are added, as the case requires, in the respective amounts not to impair the effectiveness of the present invention.

The shampoo of the present invention thus obtained, has a superior hair conditioning effectiveness and a hair washing effectiveness, and if inadvertently permitted to enter the eyes during the hair washing or rinsing, it gives less irritation than the conventional shampoo, and the influence to the mucous membrane and iris is mild.

(2) Hair rinsing compositions:

A hair rinsing composition is prepared by dissolving or dispersing the cationic keratin and cationic surfactant in a proper solvent such as water, ethanol, glycerine, ethylene glycol, propylene glycol, 1,3-propanediol, isopropanol, polyethylene glycol or the like.

The hair rinsing composition of the present invention provides good rinsing effectiveness without use of a cationic surfactant which is used in conventional hair rinsing compositions, and if such a cationic surfactant is used in addition to the cationic keratin, it presents rinsing effectiveness superior to the conventional hair rinsing compositions.

In the hair rinsing composition of the present invention, the amount of the cationic keratin is from 0.01 to 10%, preferably from 0.03 to 3%. If the amount of the cationic keratin is less than 0.01%, no adequate effectiveness is obtainable. On the other hand, if the amount exceeds 10%, there will be an undesirable phenomenon that the hair tends to be sticky under a high humidity condition. The amount of the cationic surfactant is from 0.5 to 20%, preferably from 1.0 to 10%.

The hair rinsing composition of the present invention may contain, in addition to the above mentioned cationic keratin and solvents known components commonly used in the conventional hair rinsing compositions. It is particularly preferred to incorporate a surfactant selected from an anionic surfactant, a nonionic surfactant, and an amphoteric surfactant, as an assistant component.

As such a surfactant, the following may be mentioned.

(a) Anionic surfactants (1) A straight chained or branched alkyl benzene sulfonate having an alkyl group of from 10 to 16 carbon atoms on an average.

(2) An alkyl or alkenyl ethoxy sulfate having a straight chained or branched alkyl or alkenyl group of from 8 to 20 carbon atoms and with addition of from 0.5 to 8 moles, on an average, of ethylene oxide in its molecule.

(3) An alkyl or alkenyl sulfate having an alkyl or alkenyl group of from 10 to 20 carbon atoms on an average.

(4) An olefin sulfonate having from 10 to 20 carbon atoms in its molecule.

(5) An alkane sulfonate having from 10 to 20 carbon atoms, on an average, in its molecule.

(6) A saturated or unsaturated fatty acid salt having from 10 to 20 carbon atoms, on an average, in its molecule.

(7) An alkyl or alkenyl ethoxy carboxylate having an alkyl or alkenyl group of from 10 to 20 (preferably from 12 to 16) carbon atoms, on an average, and with addition of from 0.5 to 8 moles, on an average, of ethylene oxide in its molecule.

(8) A α-sulfo fatty acid salt or ester represented by the following formula, $$R_2CHCO_2Y_2$$
$$|$$
$$SO_3M_1$$

where $Y_2$ is an alkyl group of from 1 to 3 carbon atoms or a counter ion, $M_1$ represents a counter ion and $R_2$ represents an alkyl or alkenyl group having from 10 to 20 (preferably from 12 to 16) carbon atoms.

As the counter ion for the above anionic surfactant, there may be mentioned an alkali metal ion such as sodium, or potassium, an alkaline earth metal ion such as calcium or magnesium, an ammonium ion, and an alkanolamine having from 1 to 3 alkanol groups of 2 or 3 carbon atoms (e.g. monoethanolamine, diethanolamine, triethanolamine, or triisopropanolamine).

(b) Nonionic surfactants:

(1) A polyoxyethylenealkyl or alkenyl ether having a primary or secondary alkyl or alkenyl group having from 8 to 20 carbon atoms on an average and with addition of from 3 to 12 moles of ethylene oxide.

(2) A polyoxyethylenealkylphenyl ether having an alkyl group of from 8 to 12 carbon atoms on an average and with addition of from 3 to 12 moles of ethylene oxide.

(3) A higher fatty acid alkanolamide or its alkylene oxide addition product represented by the following formula

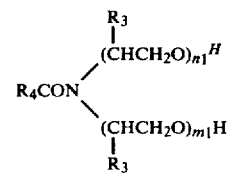

where $R_3$ represents H or $CH_3$, $R_4$ represents an alkyl or alkenyl group having from 10 to 20 carbon atoms, and $n_1$ is an integer of 1 to 3 and $m_1$ is an integer of 0 to 3.

(c) Amphoteric surfactants:

(1) An alkylamine oxide represented by the following formula

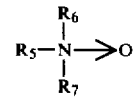

where $R_5$ is an alkyl or alkenyl group having from 10 to 20 carbon atoms, each of $R_6$ and $R_7$ is an alkyl group having from 1 to 3 carbon atoms and may be the same or different.

Among these, the one in which $R_5$ has from 12 to 16 and $R_6$ and $R_7$ are a methyl group, is preferred.

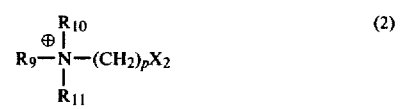

where $R_9$ represents an alkyl or alkenyl group having from 10 to 20 carbon atoms, each of $R_{10}$ and $R_{11}$ is an alkyl group having from 1 to 4 carbon atoms, p is an integer of 1 to 3, and $X_2$ represents $—COO^\ominus$ or $—SO_3^\ominus$.

Among these, the one wherein $R_9$ has from 12 to 16 carbon atoms, each of $R_{10}$ and $R_{11}$ is a methyl group, and p is 3, is preferred.

(4) An imidazoline compound represented by the following formula

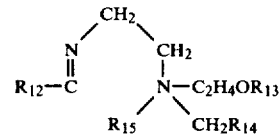

where $R_{12}$ represents a fatty acid residue having from 10 to 20 carbon atoms on an average, $R_{13}$ represents hydrogen, Na or $CH_2COOMe$ (where Me is H, Na or an organic salt group), $R_{14}$ represents COOMe, $CH_2COOMe$ or

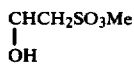

(where Me is as defined above), and $R_{15}$ represents a hydroxyl group, an acidic salt, an anionic surfactants such as alkyl sulfate or sulfonate.

Among these, the one wherein $R_{12}$ has from 12 to 16 carbon atoms, is preferred.

(d) Cationic surfactants:

As the cationic surfactant to be used in the present invention, any one which is commonly used in a hair rinsing composition may be used without any particular restriction. However, a quaternary ammonium salt represented by the following formula (I),

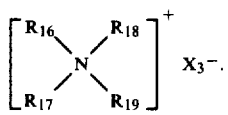

where one or two of $R_{16}$, $R_{17}$, $R_{18}$ and $R_{19}$ represent a long chained alkyl group or a long chained hydroxyalkyl group having from 8 to 20 carbon atoms, the rest represents an alkyl or hydroxyalkyl group having from 1 to 3 carbon atom or a benzyl group, and $X_3$ represents a halogen atom or an alkyl surface group having 1 or 2 carbon atoms, is preferred. Particularly preferred is distearyl dimethyl ammonium chloride, stearyl trimethyl ammonium methosulfate, stearyl trimethyl ammonium chloride, stearyl dimethyl benzyl ammonium chloride, lauryl diethyl benzyl ammonium chloride, lauryl trimethyl ammonium bromide, distearyl methyl hydroxymethyl chloride or cetyl trimethyl ammonium chloride.

Among the above mentioned surfactants, anionic surfactants are preferred, and particularly preferred is an alkylethoxy sulfate having a straight chained or branched alkyl group of from 12 to 16 carbon atoms on an average and with addition of from 1 to 4 moles of ethylene oxide in its molecule, or a straight or branched alkyl sulfate having from 12 to 16 carbon atoms on an average.

Good results are obtainable when these surfactants are incorporated in the hair rinsing compositions in an amount of from 0.01 to 10%, preferably from 0.5 to 5%.

The hair rinsing composition of the present invention may further optionally contain a hydrocarbon such as liquid paraffin, vaseline or solid paraffin, an ester such as isopropylmyristate, lanolin derivatives such as lanolin, refined lanolin or lanolin fatty acid, a silicone derivative such as dimethylpolysiloxane, methylphenylpolysiloxane or organo modified polysiloxane, an oil agent such as polyethylene glycol, polypropylene glycol, a polymer thereof, polyoxyalkylenealkyl ether or polyoxyalkylenealkyl ether phosphoric acid, a polymer substance such as hydroxyethylcellulose, hydroxypropylcellulose, hydroxypropylmethylcellulose, methylcellulose, cationic cellulose, or a cationic polymer, a bacteriocide, a preservative, a perfume and a pigment, as optional ingredients.

(3) Hair setting compositions (Hair setting lotions, hair sprays, etc.)

A hair setting composition is prepared by dissolving the cationic keratin in a polar solvent such as water, ethyl alcohol, propyl alcohol, etc. in accordance with a usual method.

The amount of the cationic keratin in the hair setting composition of the present invention is from 0.01 to 10%, preferably from 0.1 to 5%.

The hair setting composition of the present invention may further contain optional ingredients depending upon its particular purpose within a limit not to adversely affect the effectiveness of the present invention. As such optional ingredients, there may be mentioned an oily substance such as a higher alcohol, or a higher fatty acid ester; a nonionic surfactant such as polyoxyethylene lauryl ether, monolauric acid polyoxyethylene sorbitan or polyoxyethylene hydrogenated castor oil as an emulsifier or a solubilizer; a wetting agent such as glycerine or propylene glycol; a perfume and a pigment.

The hair setting composition of the present invention may be directly applied to hair, or may be applied in a form of mist with use of a pump spray. Otherwise, it may be filled in a container together with a propellant such as Freon gas, liquefied hydrocarbon or carbon dioxide and may be applied in a form of a mist or foam discharged from the container.

The hair setting composition of the present invention thus obtained, forms a uniform and strong film when dried, thus providing a superior hair setting effectiveness even in a high humidity condition, and it can readily be removed from the hair when washed with a commonly used shampoo containing e.g. an anionic surfactant. Thus, it is a superior setting composition which is capable of satisfying both requirements for setting effectiveness and washability.

(4) Pre-shampoo conditioner

A preshampoo conditioner is prepared by dissolving or dispersing the cationic keratin or the cationic keratin and a cationic polymer in a solvent such as water together with other conventional ingredients in accordance with a usual method.

The amount of the cationic keratin in the pre-shampoo conditioner is preferably from 0.01 to 5%. In a case where a cationic polymer is incorporated, the amount thereof is preferably from 0.1 to 5%. With respect to these components, if their amounts are less than the above lower limits, no adequate effectiveness is obtainable, and if their amounts exceed the above upper limits, no increase in the effectiveness is obtainable and such is economically undesirable.

As the cationic polymer to be incorporated in the pre-shampoo conditioner of the present invention, there may be mentioned, for instance, the following polymers of diallyl quaternary ammonium salts, cationic celluloses, cationic starches and cationic vinyl polymers.

(1) Polymers of diallyl quaternary ammonium salts.

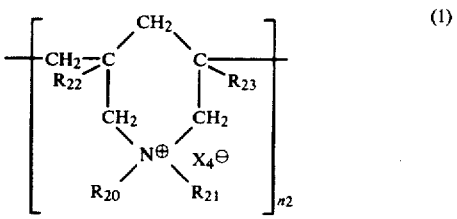

-continued

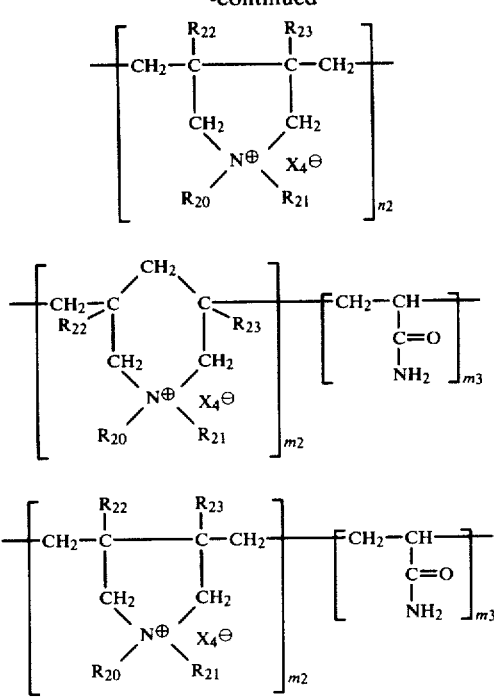

where $R_{20}$ and $R_{21}$ may be the same or different and each represents hydrogen or an alkyl group having from 1 to 18, preferably from 1 to 4, carbon atoms, $R_{22}$ and $R_{23}$ may be the same or different, and each represents hydrogen, an alkyl group having from 1 to 3 carbon atoms or a phenyl group, $X_4^\ominus$ represents an anionic residue, i.e. a halogen ion such as chlorine or bromine, an inorganic acid residue such as sulfuric acid or nitric acid residue, or an organic acid residue such as methyl sulfuric acid or hydroxycarboxylic acid, and $n_2$, $m_2$ and $m_3$ represent the numbers giving a molecular weight of from 10,000 to 1,000,000.

(2) Cationic celluloses or cationic starches

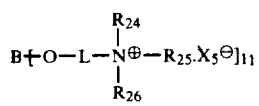

where B represents a cellulose residue or a starch residue, L represents an alkylene group or an hydroxyalkylene group, $R_{24}$, $R_{25}$ and $R_{26}$ may be the same or different and each represents an alkyl group, an aryl group or an aralkyl group, or may form a heterocyclic ring together with the nitrogen atom in the formula, $X_5$ represents an anion (such as chlorine, iodine, bromine, sulfuric acid, sulfonic acid, methyl sulfuric acid, phosphoric acid or nitric acid), and $l_1$ is an positive integer.

(3) Cationic vinyl polymers

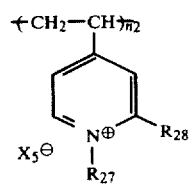

where $R_{27}$ and $R_{28}$ may be the same or different and each represents hydrogen, an alkyl having from 1 to 6 carbon atoms or a phenyl group, and $n_2$ and $X_5^\ominus$ are as defined above.

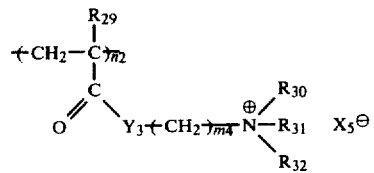

where $R_{29}$ is a hydrogen atom or a methyl group, $R_{30}$, $R_{31}$ and $R_{32}$ may be the same or different and each represents a hydrogen atom, an alkyl or substituted alkyl group having from 1 to 4 carbon atoms, $Y_3$ is an oxygen atom or a NH group in the amide bond, $X_5$ is an anion, $m_4$ is an integer of 1 to 10, and $n_2$ is as defined above.

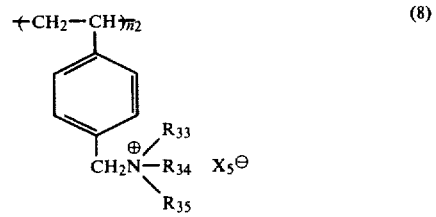

where $R_{33}$, $R_{34}$ and $R_{35}$ may be the same or different, and each represents a hydrogen atom, an alkyl or substituted alkyl group having 1 or 2 carbon atoms, $X_5$ is an anion and $n_2$ is as defined above.

Among these cationic polymers, a diallyl dimethyl ammonium homopolymer and a cationic cellulose are particularly preferred.

As other optional ingredients, there may be used an oily or fatty substance such as a higher alcohol or a fatty acid ester, a nonionic surfactant such as polyoxyalkylene alkyl ether serving as an emulsifier or solubilizer, and a wetting agent such as glycerine, pyrrolidone carboxylic acid, or propylene glycol. For instance, by the addition of such ingredients as a fatty acid ester, a liquid nonionic surfactant or polypropylene glycol, it is possible to finish the hair with an improved wettability, and by the addition of such ingredients as a solid higher alcohol, wax or silicone oil, it is possible to provide the hair with smoothness when dried. Further, by the addition of a wetting agent such as glycerine or pyrrolidone carboxylic acid, it is possible to finish the hair with an increased softness.

If shampooing is carried out after treating hair by application of the preshampoo treatment thus obtained, the damages to the hair will be minimized, and it is possible to finish the hair with an improved softness.

Especially, the pre-shampoo conditioner wherein the cationic keratin and the cationic polymer are used in combination, is very well adsorbed in the hair damaged by bleaching or permanent wave treatment, thereby to prevent damages by drying and to minimize the formation of split-ends or broken hairs, and it also gives extremely good results in the hair conditioning effectiveness.

(5) Permanent wave waving lotion:

A permanent wave agent is prepared by incorporating the cationic keratin in a permanent wave waving lotion composition containing a reducing substance as the essential material.

The permanent wave waving lotion of the present invention (hereinafter referred to "waving lotion") contains the cationic keratin in an amount of from 1 to 20%, preferably from 2 to 5%. If the amount is less than the lower limit, no adequate effectiveness for the purpose of the present invention is obtainable. On the other hand, if the amount exceeds the upper limit, the cationic keratin deposits on the hair excessively, and there will be a disadvantage that the hair tends to be sticky under a high humidity condition.

As the reducing substance constituting the base material of the waving lotion of the present invention, any one of the conventionally used reducing agents may be use. Especially preferred are an ammonium salt of tioglycollic acid, and cysteine hydrochloride.

The primary agent of the present invention can be prepared by admixing the above mentioned components by a method per se known. It is possible to further incorporate a pigment, a perfume, a oil component, a opacifier, a water soluble silicone, an organic salt, urea and the like, which are commonly used in the conventional waving lotion, depending upon the particular purposes.

(6) Permanent wave neutralyzer:

A permanent wave neutralyzer is prepared by incorporating the cationic keratin in a permanent wave neutralyzer containing an oxidizing substance as the base material.

The permanent neutralyzer (hereinafter referred to as "neutralyzer") of the present invention contains the cationic keratin in an amount of from 0.01 to 10%, preferably from 0.1 to 5%. The amount of the oxidizing substance as the base material varies depending on whether the neutralyzer is dissolved in a solvent or depending on the degree of the dilution in the case where it is used in a diluted form, and it is usually from 1 to 30%, preferably from 3 to 20%.

Further, as the oxidizing substance constituting the base material of the neutralyzer, there may be used any one of the conventionally used oxidizing substances. For instance, there may be mentioned an alkali metal salt of bromic acid such as sodium bromate or potassium bromate, hydrogen peroxide, sodium percarbonate and sodium perborate. Among them, an alkali metal salt of bromic acid is particularly preferred.

The neutralyzer of the present invention may further contain optional ingredients in addition to the above mentioned essential ingredients, in such amounts as not to adversely affect the effectiveness of the present invention. As such optional ingredients, there may be mentioned an anionic surfactant, an amphoteric surfactant, a nonionic surfactant, a cationic surfactant, a cationic polymer compound, a water soluble silicone, urea, a suitable oil agent, a wetting agent, a perfume or a pigment.

Among the optional ingredients, as a cationic polymer compound, there may be mentioned a cationic cellulose derivative, a cationic starch, a diallyl quaternary ammonium salt or a copolymer of a diallyl quaternary ammonium salt with acrylamide, a polyglycolpolyamine condensation product, a methacryloxyethyltrimethyl ammonium salt or a copolymer of a methacryloxyethyltrimethyl ammonium salt with polyvinylpyrrolidone. Particularly effective among them, are a cationic cellulose represented by a trade name "Polymer JR", a diallyl quaternary ammonium salt represented by the trade name "Merquat 100" and a diallyl quaternary ammonium salt/acrylamide co-polymer represented by the trade name "Merquat 500". The amount of the cationic polymer compound which is added, is preferably from 0.01 to 5%, particularly preferably from 0.05 to 2%.

The neutralyzer thus obtained is then adjusted for a pH so that the pH of its 5% aqueous solution becomes to be less than 9, preferably from 3.5 to 6.5.

(7) Hair dyeing compositions:

A hair dyeing composition is prepared by incorporating the cationic keratin in a base material for a hair dyeing composition.

The amount of the cationic keratin in the hair dyeing composition of the present invention is from 0.1 to 10%, preferably from 0.5 to 5%. If the amount is less than 0.1%, no adequate effectiveness is obtainable, and if the amount exceeds 10%, no further increase of the effectiveness is obtainable and there will be a disadvantage that the hair tends to be sticky under a high humidity condition. The cationic keratin is soluble in water and accordingly it can be incorporated as it is.

There is no particular limitation to the hair dyeing base material of the hair dyeing composition of the present invention, and any conventional composition may be used. For instance, an oxidation hair dyeing composition and a temporary hair dyeing composition are described as follows:

(i) Oxidation hair dyeing compositions:

A dye intermediate, an oxidizing agent and if necessary, a coupler or a modifier, are mixed.

As the dye intermediate, there may be mentioned a para component or an ortho component such as p-phenylenediamine, toluene-2,5-diamine, N-phenyl-p-phenylenediamine, 4,4'-diamino-phenylamine, p-aminophenol, p-methylaminophenol, o-phenylenediamine, toluene-3,4-diamine, o-aminophenol, p-chloro-o-phenylenediamine, p-amino-o-cresol, o-chloro-p-phenylenediamine, phloroglucin, pyrogallol, 3,3'-iminodiphenyl, diphenylamine, 2,6-diaminopyridine, or p-aminophenyl sulfamic acid. As the coupler (or modifier), there may be mentioned a meta component such as m-phenylenediamine, toluene-2,4-diamine, p-methoxy-m-phenylenediamine, m-aminophenol, α-naphthol, resolcinol, hydroquinone or catechol, or phenols. As the oxidizing agent, hydrogen peroxide is normally used, but there may be mentioned, sodium perborate, urea peroxide, sodium percarbonate, sodium peroxy tripolyphosphate, sodium peroxypyrophosphate, sodium peroxyorthophosphate, a hydrogen peroxide adduct of sodium silicate or a hydrogen peroxide adduct of sodium sulfate-sodium chloride. Further, in order to modify the color tone of the hair, a direct cotton dye, especially a nitro dye such as nitro-p-phenylenediamine, p-nitro-o-phenylenediamine, 2-amino-4-nitrophenol, 2-amino-5-nitrophenol, or 4-amino-2-nitrophenol and, if necessary, picramic acid, picric acid, or 1,4-diaminoanthraquinone, may be added, although they do not participate in the color forming reaction.

Further, a nonionic surfactant, a cationic surfactant, a solvent such as propylene glycol or glycerine, a lower alcohol such as ethyl alcohol or isopropyl alcohol, a viscosity controlling agent such as hydroxyethylcellulose, methylcellulose, a cationic polymer compound, or a higher alcohol, a wetting agent, a protein denaturing agent such as urea, a perfume, a pigment, an ultraviolet ray absorption agent, an antioxidizer, an anticeptic, a pearling agent, or a lotion forming agent, may be added in an amount not to adversely affect the effectiveness of the present invention.

The oxidation hair dye composition according to the present invention, may be prepared by mixing the above mentioned ingredients and the cationic keratin in accordance with a usual method to obtain a power or creamy formulation, which can be used by itself, i.e. by adding it to water or a shampoo. Otherwise, it is possible to prepare the oxidation dye and an oxidizing agent separately and to incorporate the cationic keratin to either one or both of them to obtain a combination of formulations such as powder formulations, creamy formulations or liquid formulations which are adapted to be mixed for use at the time of the application.

(ii) Temporary hair dyeing compositions:

There is no particular restrictions for the dye or pigment to be used. However, for instance, pigments such as titanium oxide, or carbon black and tar dyestuffs such as a triphenylmethane dye, an azo dye, a quinoline dye, a xanthene dye, an acridine dye, an azine dye, an oxazine dye, an indigoid dye, an anthraquinone dye, a stilbene dye or a thiazole dye, are mentioned.

Further as the resin, there may be used, for instance, a copolymer of an acrylic acid ester and a methacrylic acid ester, a copolymer of a monochloro acetic acid amine salt modified product of N,N'-dimethylaminoethylmethacrylate and a methacrylic acid ester, a vinylpyrrolidonevinylacetate co-polymer.

The temporary hair dyeing composition is prepared by dissolving or dispersing the cationically activated keratin and the resin, a dyestuff, a pigment, etc., in a dispersing medium such as water, amyl alcohol, isopropanol, ethanol, or acetone. It is possible to further add conventional ingredients of known temporary hair dyeing compositions depending upon the particular purposes. As such ingredients, there may be mentioned, an anionic surfactant, a cationic surfactant, an amphoteric surfactant, a nonionic surfactant, a polyalcohol such as propylene glycol, glycerine or polyethylene glycol, a higher alcohol such as isostearyl alcohol, or oleyl alcohol, a fatty acid such as a lanolin fatty acid, or a coconut fatty acid, an ester such as isopropylmyristate, a hydrocarbon such as liquid paraffin, a cationic polymer compound, an amine, and a perfume.

The temporary hair dyeing composition containing the cationic keratin may be made in an optional formulation such as a mascara type, spray type or lotion type formulation.

The hair treating cosmetics of the present invention obtained by the foregoing manners, overcome the drawbacks inherent to the conventional hair treating cosmetics, present superior hair conditioning effectiveness, prevent the damage or degradation of the hair, and give good texture upon application.

Now, the present invention will be described with reference to Examples and Comparative Examples. However, the present invention is not restricted to these Examples.

EXAMPLE 1

10 g of wool fibers were immersed in 700 g of a 50% n-propanol aqueous solution containing 0.02 M of a Tris buffer solution, 4 ml of tri-n-butylphosphine was added as a reducing agent, the pH was adjusted to be 8.0 with 1 N hydrochloric acid, and the reduction reaction was carried out at room temperature for 24 hours under circulation of nitrogen. Then, 1.5 g of glycidyl trimethyl ammonium chloride was added to the reaction system, and stirred at 70° C. for 5 hours, whereupon about 85% of the wool fibers dissolved in the reaction solution. The non-dissolved fibers were removed by filtration, and the filtrate thereby obtained was subjected to ultrafiltration (with use of a membrane having a fractional molecular weight of 1000) to remove low molecular weight impurities such as the reducing agent and at the same time to concentrate the whole system to about 150 ml. The concentrate was freeze-dried whereupon 8.1 g of solid powder was obtained. The molecular weight of the solid powder was found to be 39,000 by a gel filtration method (with use of Cephadex G-75). On the other hand, the solid powder was subjected to hydrolysis in 6 N hydrochloric acid at 110° C. for 24 hours, the decomposed products were subjected to an amino acid analysis (with use of Hitachi Automatic Amino Acid Analyser Type KLA-5), and the results thereby obtained were compared with the results of the amino acid analysis of the starting wool fibers, whereby as shown in Table it was found that the amino acid compositions and contents except for cystine, were almost the same between them, but with respect to cystine, 5.5 moles of cystine was observed in 100 moles of the amino acids of the wool, while no cystine was observed in the solid powder, thus indicating an addition of glycidyl trimethyl ammonium chloride. Thus, from the results obtained by the amino acid analysis and the molecular weight determination, it was found that the solid powder thus obtained did not undergo any change in the peptide bonds in the main chain of the keratin protein by the hydrolysis and that the disulfide bonds were split and β-hydroxy-γ-trimethyl ammoniopropyl group was added to form S-(β-hydroxy-γ-trimethyl ammoniopropyl) keratein.

TABLE

| Results of the amino acid analysis [a] | | |
|---|---|---|
| Amino acids | Wool fibers [b] | Solid powder [c] |
| Lysine | 2.6 | 2.7 |
| Histidine | 0.7 | 0.7 |
| Alginine | 6.5 | 5.9 |
| (½) Cystine | 11.0 | 0 |
| Aspartic acid | 6.1 | 6.7 |
| Threonine | 6.4 | 5.7 |
| Serine | 10.7 | 11.2 |
| Glutamic acid | 12.9 | 13.6 |
| Proline | 6.3 | 6.3 |
| Glycine | 8.2 | 8.4 |
| Alanine | 5.8 | 6.5 |
| Valine | 5.6 | 4.7 |
| Methionine | 0.7 | 0.5 |
| Isoleucine | 3.1 | 3.1 |
| Leucine | 6.9 | 8.0 |
| Tyrosine | 3.5 | 3.3 |
| Phenylalanine | 3.0 | 2.7 |

Notes:
[a] Tryptophane was decomposed under the hydrolysis conditions employed, and was not analyzed.
[b] The unit is by moles in 100 moles of amino acids.
[c] The unit is by moles in 90 moles of amino acids (Since the cystine content was found to be zero, the unit was set in this manner in order to facilitate the comparison with the results of the wool fibers as the starting material.)

EXAMPLE 2

10 g of wool fibers were immersed in 600 g of an aqueous solution containing 0.02 M of a Tris buffer solution, 6.0 ml of 2-mercaptoethanol was added as a reducing agent, then the pH was adjusted to be 8.5 with 1 N hydrochloric acid, and the reduction reaction was carried out at room temperature for 24 hours under circulation of nitrogen. Then, 2.0 g of glycidyl trimethyl ammonium chloride was added to the reaction system, and stirred at 50° C. for 6 hours, whereupon about 80% of the wool fibers dissolved in the reaction solution. The non-dissolved fibers was removed by filtration, and from the aqueous solution of the cationic keratin compound thus obained, lower molecular weight impurities such as the reducing agent were removed by superfiltration and at the same time, the aqueous solution of the cationic keratin compound was concentrated to about 1/5. The concentrate was freeze-dried, whereupon 7.5 g of the cationic kerain compound derivative was obtained. The average molecular weight of the product was found to be 41,000 by a gel filtration method.

EXAMPLE 3

The same operation as in Example 2 was carried out except that the reaction solvent in Example 2 was replaced by a 50% n-propanol aqueous solution, and as the reducing agent, 4 ml of tri-n-butylphosphine was used, whereupon 7.8 g of a cationic keratin derivative having an average molecular weight of 40,000 was obtained.

EXAMPLE 4

10 g of wool fibers were immersed in 700 g of a 30% ethanol aqueous solution containing 0.02 M of a Tris buffer solution, 4 ml of tri-n-bytylphosphine was added as a reducing agent, then the pH was adjusted to be 8.0 with 1 N hydrochloric acid, and the reduction reaction was carried out at room temperature for 24 hours under circulation of nitrogen. Then, 2.5 g of allyl trimethyl ammonium chloride was added to the reaction system, and stirred at 70° C. for 5 hours, whereupon about 85% of the wool fibers dissolved in the reaction solution. The non-dissolved fibers were removed by filtration, and the filtrate thereby obtained was subjected to ultrafiltration (with use of a membrane having a frictional molecular weight of 1,000) to remove low molecular weight impurities such as the reducing agent, and at the same time to concentrate the whole system to about 150 ml.

The concentrate was freeze-dried, whereupon 8.2 g of a cationic keratin having an average molecular weight of 39,000 was obtained.

EXAMPLE 5

Feathers were heated in a pressure-resistant container of 6 Kg/cm$^2$ with a super-heated steam at 240° C. for 6 minutes, and abruptly discharged in the atmosphere to obtain a porous putted product, 10 g of the putted product was immersed in 700 g of a 30% ethanol aqueous solution containing 0.02 M of a Tris buffer solution, 4 ml of tri-n-butylphosphine was added as a reducing agent, then the pH was adjusted to be 8.0 with 1 N hydrochloric acid, and the reduction reaction was carried out at room temperature for 24 hours under circulation of nitrogen. Then, 2.5 g of allyltrimethyl ammonium chloride was added to the reaction system, and stirred at 70° C. for 5 hours, whereupon about 90% of the expanded feather product dissolved in the reaction solution. The non-dissolved feathers were removed by filtration, and the filtrate thereby obtained was subjected to ultrafiltration to remove low molecular weight impurities such as the reducing agent and at the same time to concentrate the filtrate to about 150 ml. The concentrate was freeze-dried whereupon 8.5 g of a cationic keratin having an average molecular weight of 38,000 was obtained.

EXAMPLE 6

10 g of wool fibers were immersed in a 1% sodium sulfite aqueous solution, the pH was adjusted to be 6.7 with a 5 N sodium hydroxide aqueous solution, then 0.2 g of papain was added, and hydrolysis was carried out at 60° C. for 15 hours, whereupon about 80% of the wool fibers dissolved in the reaction solution. The non-dissolved fibers were removed by filtration, and the sulfite in the filtrate thereby obtained was removed by ultrafiltration with use of a membrane having a fractional molecular weight of 500, and at the same time, the aqueous solution of the hydrolyzed products was concentrated. The concentrate was freeze-dried, whereupon 7.7 g of hydrolyzed products having a molecular weight of 2,000 were obtained.

The products were dissolved in 450 g of an aqueous solution containing 0.02 M of a Tris buffer solution, 4.5 ml of 2-mercapto-ethanol was added as a reducing agent, then the pH was adjusted to 8.5 with 1 N hydrochloric acid, and the reduction reaction was carried out at room temperature for 18 hours under circulation of nitrogen. Then, 16 g of glycidyl trimethyl ammonium chloride was added to the reaction system, and stirred at 50° C. for 6 hours. Lower molecular weight impurities such as the reducing agent were removed by ultrafiltration from the reaction solution thereby obtained, and the aqueous solution was concentrated to about 1/5. The concentrate was freeze-dried, whereupon 6.2 g of a cationic keratin was obtained.

EXAMPLE 7

Wool was heated in a high pressure container with a saturated steam under a pressure of 4 Kg/cm$^2$ for 8 minutes, and abruptly discharged into the atmosphere, whereupon a porous putted product was obtained. 10 g of this putted product was immersed in 300 g of a 75% phosphoric acid aqueous solution and stirred at a temperature of 120° to 130° C. for 5 hours, whereby hydrolysis was carried out. The solution was cooled, the non-dissolved component was removed by filtration, then water in an amount of from 4 to 5 times was added, and the non-dissolved component was further removed by centrifugation. Then, the pH was adusted to 6.7 by adding calcium carbonate, and the precipitates were collected by filtration and dried, whereupon 8.5 g of hydrolyzed products having a molecular weight of 2,000 were obtained.

The hedrolyzed products were dispersed in 500 g of an aqueous solution containing 0.02 M of a Tris buffer solution, 4 ml of tri-n-butylphosphine was added as a reducing agent, then the pH was adjusted to 8.0 with 1 N hydrochloric acid, and the reduction reaction was carried out for 24 hours under circulation of nitrogen. Then, 20 g of glycidyl trimethyl ammonium chloride was added to the reaction system, and stirred at 50° C. for 6 hours. Low molecular weight impurities such as the reducing agent were removed by ultrafiltration from the reaction solution thereby obtained, and the aqueous solution was concentrated, and freeze-dried, whereupon 6.7 g of a cationic keratin was obtained.

EXAMPLE 8

In a manner similar to Example 6, a reaction was carried out with use of 10 g of a puffed product of feathers instead of the wool fibers and 20 g of 2-chloro-2-hydroxypropyltrimethyl ammonium chloride instead of glycidyl trimethyl ammonium chloride, whereupon a cationic keratin was obtained.

EXAMPLE 9: SHAMPOOS

With use of cationic keratins synthesized in Examples 1 to 8, shampoo compositions having the below mentioned constitution were prepared, and their properties were tested. The results thereby obtained are shown in Table 1.

The evaluation of the properties in this Example was made in accordance with the following methods.

(1) Foaming test 0.1% of lanolin was added as artificial soil to an aqueous solution containing 1% of the shampoo composition and stirred in a cylinder with a flat stirrer at 40° C. at a speed of 1,000 rpm for 5 minutes with reversion of the rotation every 10 seconds. The evaluation was made for the amount of foaming after 30 seconds from the completion of the stirring.

(2) Texture of foams

A tress of 30 g of human hair was wet with water of 40° C. and 20 g of the water was thereby absorbed. Then, the hair was washed with 1 g of the shampoo composition, and the texture of the foam was determined on the basis of the sensory evaluation by 20 female panelists. The item for the evaluation The smoothness in passing the fingers through the hair at the time of washing hair was evaluated as the "foam smoothness".

The standards for the evaluation o: The foam smoothness is distinctly better than the standard shampoo.

Δ: The foam smoothness is slightly better than the standard shampoo.

x: The foam smoothness is equivalent to the standard shampoo.

| Standard Shampoo | |
|---|---|
| Sodium polyoxyethylene (3) Lauryl sulfate | 15% |
| Coconut fatty acid diethanol amide | 3% |
| Perfume | q.s. |
| Water | Balance (pH: 7.2) |

(3) Combing ease

A tress of 30 g of human hair was wet with water of 40° C. and 20 g of the water was thereby absorbed. The hair was washed with 1 g of the shampoo composition, then rinsed twice and the excess squeezed. In the squeezed state, the hair which was connected to a strain gauge, was combed with use of a comb and the force exerted at that time was measured (in a wet condition). The hair was then dried with use of a drier and then left to stand still in a constant temperature and humidity chamber at 20° C. under a relative humidity of 65% for one night. Then, the hair connected to the strain gauge was combed with a comb and the force exerted at that time was measured (in a dried condition).

(4) Hair-fly

At the time of measuring the combing ease in the dried condition, an observation was made as to whether a hair-fly phenomenon occurs due to static electricity. Standards for the evaluation o: The hair-fly phenomenon occurs.

x: The hair-fly phenomenon does not occur.

| Composition | |
|---|---|
| Sodium polyoxyethylene (2) lauryl Sulfate | 15% |
| Cationic keratin (see Table 1) | 3% |
| Water | Balance |

Results

TABLE 1

| | Foam characteristics | | Finished hair | |
|---|---|---|---|---|
| Cationic keratins | Foaming (ml) | Foam smoothness | Combing ease | Hair-fly |
| The one obtained in Example 1 | 180 | ⊙ | 80 | ⊙ |
| The one obtained in Example 2 | 174 | ⊙ | 100 | ⊙ |
| The one obtained in Example 6 | 172 | ⊙ | 90 | ⊙ |
| The one obtained in Example 7 | 175 | ⊙ | 100 | ⊙ |
| None | 114 | x | 210 | x |

EXAMPLE 10: HAIR RINSING COMPOSITIONS

Hair rinsing compositions having the following compositions were prepared with use of the cationic keratin obtained in Example 3.

Each of these hair rinsing compositions was diluted 50 times, and hair was treated with 500 ml of the diluted solution, then rinsed twice with warm water and air-dried. Composition (A) was compared with Compositions (B) and (C) according to Scheffe's paired comparison method by 20 panelers and evaluated in 5 grades. The results thereby obtained are shown in Table 2.

| Compositions: | | |
|---|---|---|
| (A): | Distearyl dimethyl ammonium chloride | 2.0 (%) |
| | Monostearyl trimethyl ammonium chloride | 0.5 |
| | Cationic keratin of Example 3 | 0.1 |
| | Water | Balance |
| (B): | Distearyl dimethyl ammonium chloride | 2.0 (%) |
| | Monostearyl trimethyl ammonium chloride | 0.5 |
| | Alkaline hydrolyzed product of collagen (MW: 800 to 1,000) | 0.1 |
| | Water | Balance |
| (C): | Distearyl dimethyl ammonium chloride | 2.0 (%) |
| | Monostearyl trimethyl ammonium chloride | 0.5 |
| | Water | Balance |

TABLE 2-A

Results:
Comparison of Composition (A) (product of the present invention) and Composition (B)

| Items | Composition (A) is better | Slightly better | Almost equal | Composition (B) is slightly better | Better |
|---|---|---|---|---|---|
| Softness | 2 | 15 | 2 | 1 | 0 |
| Smoothness | 3 | 13 | 3 | 1 | 0 |
| Combing ease | 2 | 10 | 5 | 3 | 0 |

TABLE 2-B

Comparison of composition (A) (product of the present invention) and Composition (C).

| Items | Composition (A) is better | Slightly better | Almost equal | Composition (C) is slightly better | Better |
|---|---|---|---|---|---|
| Softness | 6 | 10 | 3 | 1 | 0 |
| Smoothness | 7 | 9 | 2 | 2 | 0 |
| Combing ease | 7 | 8 | 4 | 1 | 0 |

EXAMPLE 11: HAIR CONDITIONERS

Hair conditioners having the following compositions were prepared with use of cationic keratins synthesized in Examples 6 and 8, and silicone derivatives, and their hair protecting effectiveness was investigated. The hair protecting effectiveness was tested by dispersing 5 g of each of the hair conditioners in 500 ml of deionized water, immersing therein a tress of human hairs having a length of 20 cm and a weight of 5 g for 5 minutes, thereafter rinsing the hair for 5 minutes with running water, drying it, then combing it 500 times with a nylon brush, and measuring the weight of broken hairs formed by the combining.

| Composition: | |
|---|---|
| Cationic keratin (see Table 3) | 1.0% |
| Silicone derivative (see Table 3) | 3.0% |
| Water | Balance |

TABLE 3

| | Results: | |
|---|---|---|
| Cationic keratins | Silicone derivatives | Weight of broken hairs (g) |
| The one obtained in Example 6 | Dimethyl polysiloxane* | 0.060 |
| The one obtained in Example 7 | Epoxy modified silicone oil** | 0.056 |
| The one obtained in Example 8 | Dimethyl polysiloxane* | 0.083 |
| None | Dimethyl polysiloxane* | 0.370 |

Notes:
*Dimethyl polysiloxane:
(CH$_3$)$_3$SiO[(CH$_3$)$_2$SiO]$_{200}$Si(CH$_3$)$_2$
**Epoxy modified silicone oil

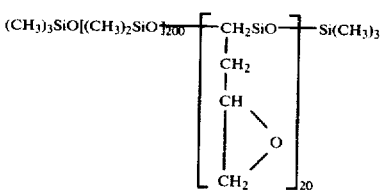

EXAMPLE 12: HAIR SETTING COMPOSITIONS

Hair setting compositions having the following composition were prepared and their hair set efficiency was investigated. The results thereby obtained are shown in Table 4.

| Composition: | |
|---|---|
| Cationic keratin (see Table 4) | 1% |
| Ethanol | 10% |
| Water-soluble silicone* | 0.5% |
| Perfume | 0.1% |
| Water | Balance |

Note:
*Polyether modified silicone oil:

$$(CH_3)_3SiO[(CH_3)_2SiO]_{n_3}\begin{bmatrix} CH_3SiO \\ | \\ (CH_2)_3 \\ | \\ (OC_2H_4)_{l_2}-(OC_3H_6)_{l_3}CH_3 \end{bmatrix}_{m_4} Si(CH_3)_3$$

where $n_3$ is 25, $m_4$ is 10, and $l_2$ and $l_3$ are 20.

Measuring method (1) Curl retention

A tress of hairs composed of human hairs of a Japanese and having a length of 14 cm and a weight of 2 g was applied with 1 g of each of the hair setting compositions listed in Table 4, wound on a glass rod having a diameter of 2.1 cm, and dried for 24 hrs. in a desiccator containing phosphorus pentoxide. After drying completely, the hair was dismounted from the rod and suspended in a constant humidity chamber at a temperature of 20° C. under a relative humidity of 95%, the length of the formed curls was measured after 30 minutes, and the curl retention was determined in accordance with the following formula.

$$\text{Curl retention (\%)} = \frac{Lo - Lt}{Lo - Ls} \times 100$$

Lo = 14 (cm)

Ls = The length (cm) of the curls immediately after suspending the hair under a relative humidity of 95%.

Lt = The length (cm) of the curls upon expiration of 30 minutes after suspending the hair under a relative humidity of 95%.

TABLE 4

| Cationic keratins | Curl retention (%) |
|---|---|
| The one obtained in Example 1 | 82 |
| The one obtained in Example 2 | 80 |
| The one obtained in Example 3 | 85 |
| The one obtained in Example 4 | 79 |
| The one obtained in Example 5 | 81 |
| Acid hydrolyzed product of collagen (MW: 15,000) | 53 |

EXAMPLE 13: BLOW-STYLING COMPOSITION

A blow-styling composition having the following composition was prepared, and its hair set efficiency, the texture of the finishing, and the residual texture after hair washing were compared with a comparative product in accordance with a paired comparison method by an evaluation panel composed of 30 females of from 18 to 35 years old. The results thereby obtained are shown in Table 5.

| Composition: | |
|---|---|
| Cationic keratin of Example 1 | 2% |
| 2-Amino-2-methyl-1-propanol | 1% |
| Ethanol | 10% |
| Water-soluble silicone (polyether modified silicone oil) | 0.5% |
| Perfume | 0.1% |
| Water | Balance |
| (Comparative product) | |

-continued

| | |
|---|---|
| Vinyl acetate-crotonic acid copolymer | 2% |
| Triisopropanolamine | 1% |
| Acid hydrolyzed product of collagen (MW: 20,000) | 0.3% |
| Ethanol | 10% |
| Water | Balance |

TABLE 5

| | Results: | | |
|---|---|---|---|
| | Items | | |
| Evaluation | Hair set efficiency | Finish texture | Residual texture |
| Product of the present invention is better | 11 | 12 | 20 |
| Product of the present invention is slightly better | 16 | 15 | 8 |
| Almost equal | 2 | 3 | 2 |
| Comparative product is slightly better | 1 | 0 | 0 |
| Comparative product is better | 0 | 0 | 0 |

EXAMPLE 14: PRE-SHAMPOO CONDITIONERS

Pre-shampoo conditioners compositions having the following composition and containing cationic keratins obtained in Examples 1 to 8 and other peptides, were prepared, and their efficiency was evaluated. The results thereby obtained are shown in Table 6.

| Composition: | |
|---|---|
| Cationic keratin (or other peptide) | 3.0% |
| Polyoxyethylene (10) cetyl ether | 2.0% |
| Hydroxyethylcellulose | 1.0% |
| Propylene glycol | 5.0% |
| Water | Balance |

Evaluation method (1) Hair texture during hair washing

A tress of hairs composed of hairs of a Japanese female and having a length of 20 cm and a weight of 20 g was applied with 2 g of the pre-shampoo composition, and left to stand for 5 minutes. Then, 2 g of a commercially available plain shampoo containing an anionic surfactant was applied and foamed for one minute in a usual manner, and the hair texture during the foaming was evaluated by a sensory test.

The sensory test was made with use of a tress of hairs treated with a commercially available pre-shampoo conditioner containing lanolin as the major component, as the standard, and in accordance with a paired comparison method, and the following evaluation points were used. (Average evaluation points by a panel of 20 specialists are shown in the Table.)

| Evaluation points | Evaluation |
|---|---|
| +2 | The texture is better than the standard tress of hairs. |
| +1 | The texture is slightly better than the standard tress of hairs. |
| 0 | The texture is equivalent to the standard tress of hairs. |
| −1 | The texture is slightly inferior to the standard tress of hairs. |
| −2 | The texture is inferior to the standard tress of hairs. |

TABLE 6

| | | Results: | | | |
|---|---|---|---|---|---|
| | | Textures of the hairs | | | Combing |
| Cationic keratins (or other peptides) | | During washing | After washing | After drying | ease (after drying) |
| Products of the present invention | The one obtained in Example 2 | +1.8 | +1.7 | +1.7 | +1.5 |
| | The one obtained in Example 3 | +1.7 | +1.6 | +1.6 | +1.5 |
| | The one obtained in Example 5 | +1.7 | +1.7 | +1.4 | +1.4 |
| | The one obtained in Example 7 | +1.7 | +1.6 | +1.5 | +1.6 |
| | The one obtained in Example 8 | +1.6 | +1.5 | +1.4 | +1.4 |
| Comparative products | Non-cationic hydrolyzed product of keratin in Example 6 | +0.3 | +0.3 | +0.3 | +0.4 |
| | Acid hydrolyzed Product of collagen (MW: 10,000 to 20,000) which has been cationized under the same conditions as in Example 2 | +0.9 | +1.0 | +0.8 | +0.9 |
| Controls | None | +0.1 | −0.2 | 0 | 0 |
| | No treatment | −0.3 | 0 | 0 | 0 |

EXAMPLE 15: PRE-SHAMPOO CONDITIONERS

Pre-shampoo type hair treating compositions as shown below, were prepared with use of cationic keratins.

| Product 1 of the present invention | |
|---|---|
| Poly (dimethyl-diallyl ammonium chloride) | 1.0% |
| Cationic keratin of Example 2 | 2.0% |

-continued

| | |
|---|---|
| Polyoxyethylene (10) oleyl ether | 1.0% |
| Hydroxyethylcellulose | 0.5% |
| Ethanol | 5.0% |
| Water | Balance |

Product 2 of the present invention

| | |
|---|---|
| Cationic cellulose JR-400 (Union Carbide Co, USA) | 1.0% |
| Cationic keratin of Example 6 | 3.0% |
| Polyoxyethylene (10) oleyl ether | 1.0% |
| Hydroxyethylcellulose | 0.5% |
| Ethanol | 5.0% |
| Water | Balance |

Comparative product 1

The same as Product 1 of the present invention except that poly (dimethyl-diallyl ammonium chloride) was omitted.

Comparative product 2

The same as Product 2 of the present invention except that cationic cellulos JR-400 was omitted.

These compositions was applied to (1) bleached hairs and (2) cold permanent waved hairs. The textures of the hairs with their applications were evaluated in 5 grades by an evaluation panel composed of 30 females of from 18 to 35 years old, in accordance with a paired comparison method. The results thereby obtained are shown in Table 7 and Table 8.

TABLE 7

| Hairs | Items | Product 1 of the present invention is better | Product 1 of the present is slightly better | Almost equal | Comparative product 1 is slightly better | Comparative product 1 is better |
|---|---|---|---|---|---|---|
| Bleached hairs | Texture after hair washing | 11 | 14 | 5 | 0 | 0 |
| | Texture after drying | 13 | 13 | 4 | 0 | 0 |
| | Combing efficiency after drying | 9 | 16 | 5 | 0 | 0 |
| Cold waved hairs | Texture after hair washing | 15 | 11 | 4 | 0 | 0 |
| | Texture after drying | 16 | 10 | 4 | 0 | 0 |
| | Combing efficiency after drying | 14 | 13 | 3 | 0 | 0 |

TABLE 8

| Hairs | Items | Product 2 of the present invention is better | Product 2 of the present invention is slightly better | Almost equal | Comparative product 2 is slightly better | Comparative product 2 is better |
|---|---|---|---|---|---|---|
| Bleached hairs | Texture after hair washing | 10 | 14 | 6 | 0 | 0 |
| | Texture after drying | 12 | 12 | 6 | 0 | 0 |
| | Combing efficiency after drying | 9 | 14 | 7 | 0 | 0 |
| Cold waved hairs | Texture after hair washing | 16 | 11 | 3 | 0 | 0 |
| | Texture after drying | 16 | 10 | 4 | 0 | 0 |
| | Combing efficiency after drying | 15 | 12 | 3 | 0 | 0 |

EXAMPLE 16: PERMANENT WAVE WAVING LOTION

Permanent wave treatment was conducted with use of a permanent wave waving lotion and neutralyzer having the following respective compositions, and the waving efficiency, wave retention, adsorption property and texture were investigated. The results thereby obtained are shown in Table 9.

| Composition: | |
|---|---|
| (1) Permanent wave waving lotion | |
| [Formulation 1 (Prodcut of the present invention)] | |
| Ammonium salt of thioglycolic acid, | 7.0% |
| Cationic keratin of Example 6 | 3.0% |
| Water (aqueous ammonium solution, for pH control) | 90.0% |
| [Formulation 2, (Comparative product)] | |
| The cationic keratin of Formulation 1 was replaced by water. | |
| (2) Permanent wave neutralyzer | |
| Sodium bromate | 5.0% |
| Water | 95.0% |

Test method (1) Waving efficiency and wave retention measuring test.

(i) A tress of 20 hairs was secured to cylindrical poles of a wave measuring plate (A plate on which slender cylindrical poles having a diameter of 2 mm and a length of 1.5 cm were arranged and fixed in two rows in a staggered fashion), and immersed in the waving lotion, i.e. Formulations 1 to 2, at 30° C. for 10 minutes, then in the neutralyzer at 30° C. for 10 minutes. After rinsing it sufficiently with water, it was dismounted from the wave measuring plate, and place in water, and the waving efficiency was calculated in accordance with the following formula.

The hairs used were those prepared by washing virgin hairs having a length of 20 cm with an aqueous solution containing 0.5% of sodium lauryl sulfate and drying them.

$$\text{Waving efficiency (\%)} = \frac{X - Z}{X - Y} \times 100$$

X: the length of the hairs secured between two points A and B which are distanced in one of the rows of the cylindrical poles arranged in a staggered fashion.

Y: the distance between A and B

Z: the distance between points on the hairs placed in water after dismounted from the measuring plate, said points having been in contact with A and B, respectively.

(ii) The hairs used in (i) were immersed in an aqueous solution containing 0.5% of sodium lauryl sulfate and gently moved for 1 minute for washing in the solution, and thereafter, the hairs were sufficiently rinsed and dried for a day in air. This operation was repeated 4 times, and after the washing of the fifth operation, the hairs were sufficiently rinsed, and placed in water, and the above mentioned Z was measured in the water and compared with the waving efficiency prior to the washing thereby to obtain a wave retention.

Wave retention (%) =

$$\frac{\text{waving efficiency after the 5th washing}}{\text{waving efficiency before the washing}} \times 100$$

(2) Adsorption property

The hairs used for the waving efficiency measurement were observed by a scanning type electron microscope and the presence or absence of the adsorbed substance on the surface of the hairs was determined. The degrees of the adsorption were evaluated in 3 grades. The evaluation standards are as shown below.

| Degrees of adsorption | The states of the surface of the hairs |
|---|---|
| + + | Covered with a film coating and being smooth. |
| + | A small amount of the adsorbed substance was observed and the surface was smooth. |
| − | Roughened and peeling-off of hair cuticle was observed. |

(3) Evaluation of textures

A tress of virgin hairs of a Japanese was immersed in the waving lotion, i.e. Formulations 1 to 2, at 30° C. for 10 minutes, and then in the neutralyzer at 30° C. for 10 minutes. The hair tress was sufficiently rinsed and dried in air. The texture of the hair tress was evaluated in 5 grades by 20 females.

The evaluation standards were excellent (point 5), good (point 4), fair (point 3), slightly inferior (point 2), and inferior (point 1), and the results were represented by accumulated average values.

TABLE 9

| Permanent wave waving lotion | Adsorption property | Results: Wave efficiency (%) | Wave retention (%) | Evaluation of textures |
|---|---|---|---|---|
| Formulation (1) | + | 56 | 87 | 3.5 |
| Formulation (2) | − | 52 | 73 | 2.4 |

EXAMPLE 17: PERMANENT WAVE NEUTRALYZER

Permanent wave treatment was conducted with use of waving lotion and neutralyzer having the following compositions, and the degrees of the damages imparted to the hairs during the treatment were determined by measurement of the changes in weight of the hairs before and after the treatment. The hair weight measuring method and the evaluation standards were as shown below:

| Compositions: | |
|---|---|
| (Formulation of the waving lotion | |
| Thioglycolic acid | 7.0% |
| Polyoxyethylene hydrogenated castor oil | 1.0% |
| Perfume | 0.2% |
| Aqueous ammonium solution, water (The pH was adjusted to 9.0 with the aqueous ammonium solution) | Balance |
| (Formulation of the neutralyzer) | |
| Base materials for the neutralyzer | |
| Sodium bromate | 5.0% |
| Amphoteric surfactant ("Miranol C2M-SF" made by Miranol Co.) | 0.5% |
| Cationic cellulose ("Polymer JR400" made by UCC Co.) | 0 or 0.5% |
| Perfume | 0.1% |
| Cationic keratin (see Table 10) | 2.0% |
| Water | Balance |

Hair weight measuring method:

Virgin hairs having a length of 10 cm were washed with a 0.5% aqueous solution of sodium lauryl sulfate and dried in air, and they were used as the test hairs. About 1 g of the hairs were bundled, and placed in a desiccator containing phosphorus pentoxide as a drying agent and dried under vaccuo for further one week, whereupon the hair weight was measured and designated as the dry weight of the virgin hairs. Then, these hairs were immersed in the waving lotion at 30° C. for 10 minutes, rinsed sufficiently with water and then immersed in the permanent wave neutralyzer at 30° C. for 10 minutes. After rinsing sufficiently with water and dried in air, the hairs were further dried in the above mentioned manner, whereupon the weight of the dried hairs was measured and designated as the dry weight of the permanent wave hairs.

Evaluation standards:

| Evaluation | Contents |
|---|---|
| ⊚ | The difference in the dry weights of the virgin hairs and the permanent wave hairs is less than 1%. |
| o | The difference in the dry weights of the virgin hairs and the permanent wave hairs is more than 1% and less than 5%. |
| X | The difference in the dry weights of the virgin hairs and the permanent wave hairs is at least 5%. |

TABLE 10

| | Results: | |
|---|---|---|
| | Evaluation Cationic cellulose | |
| Cationic keratins | 0% | 0.5% |
| The one obtained in Example 1 | o | ⊚ |
| The one obtained in Example 2 | o | ⊚ |
| The one obtained in Example 3 | o | ⊚ |
| None | X | X |

EXAMPLE 18: HAIR DYEING COMPOSITIONS

Two liquid type hair dyeing compositions having the following compositions were prepared, and their influences to the hairs were determined by measuring and evaluating the changes in weight of the hairs before and after the hair dyeing treatments. The results thereby obtained are shown in Table 11.

Compositions:

| (Color lotion composition) | |
|---|---|
| p-Phenylene diamine | 1.0% |
| Cationic keratin (see Table 11) | 1.0 or 5.0% |
| Propylene glycol | 10.0% |
| Disodium edetoic acid | 0.3% |
| Sodium sulfite | 0.5% |
| Perfume | 0.1% |
| Water | Balance |
| (The pH was adjusted to 10.0 with an aqueous ammonium solution.) | |
| (Oxidizer composition) | |
| Hydrogen peroxide | 6.0% |
| Water | 94.0% |

Evaluation method:

Virgin hairs having a length of 10 cm were washed with a 0.5% aqueous solution of sodium lauryl sulfate and dried in air, and the hairs thus obtained were designated as the test hairs. About 1 g of these hairs were bundled, placed in a desiccator containing phosphorus pentoxide as a drying agent, and further dried under vaccuo for one week, whereupon the weight of the hairs was measured and designated as the dry weight of the virgin hairs.

Then, the test hairs were subjected to hair dyeing treatment in the following manner, then dried in air, and further dried in the above mentioned manner, whereupon the weight of the dried hairs was measured and designated as the dry weight of the hair dye treated hairs.

The hair weight after the hair dyeing treatment was compared with the virgin hairs and evaluated according to the following evaluation standards, and thus, the influences of the hair dyeing composition over the hairs were determined.

Evaluation standards:

| Evaluation | Contents |
|---|---|
| ⊚ | The weight was increased over the hair weight before the treatment. |
| o | The weight was decreased by from 0 to 3% from the hair weight before the treatment. |
| X | The weight was decreased by more than 3% from the hair weight before the treatment. |

Hair dyeing treatment method:

The color lotion composition and the oxidizer composition were mixed in equal amounts to obtain a mixed solution as the hair dyeing composition, which was then diluted in a bath ratio of 1:5. In the solution thus obtained, the hairs were immersed at room temperature for 30 minutes and dyed. Then, the hair dyeing composition was washed off with a city water of 40° C., and the hairs was washed with a 0.5% aqueous solution of sodium lauryl sulfate, and after instantly immersed in a 1 N acetic acid aqueous solution, again washed with a city water of 40° C.

TABLE 11

| | Results: | | |
|---|---|---|---|
| | Cationic activated keratins | Amounts incorporated | |
| | | 1% | 5% |
| Products of the present invention | The one obtained in Example 1 | o | |
| | The one obtained in Example 2 | o | |
| | The one obtained in Example 3 | o | |
| | The one obtained in Example 4 | o | |
| | The one obtained in Example 5 | o | |
| | The one obtained in Example 6 | o | |
| | The one obtained in Example 7 | o | |
| | The one obtained in Example 8 | o | |
| Comparative products | Oxidation decomposition products of wool in an alkaline solvent (Molecular weight: 50,000) | X | X |
| | Alkali hydrolyzed products of collagen (Molecular weight: 2,000) | X | X |
| Control | No addition | X | |

EXAMPLE 19: HAIR DYEING COMPOSITIONS

Mascara type temporary hair dyeing compositions (Hair colouring agents) having the following composition were prepared. 0.5 g of each of them was applied to 1 g of white hairs and dried in air. The texture, luster and smoothness of the hairs were evaluated by a panel of 10 specialists. The results thereby obtained are shown in Table 12.

| Composition: | |
|---|---|
| Polymer resin* | 12.0% |
| Pigment (carbon black) | 1.0% |
| Cationic keratin (see Table 12) | 1.0% |
| Perfume | 0.1% |
| Ethanol | Balance |

Note:
*Polymer resin: Copolymer of an ammonium monochloro acetate modified product of N,N'—dimethylaminoethyl methacrylate and methacrylic acid ester.

TABLE 12

| | | Results: Evaluated items | | |
|---|---|---|---|---|
| Cationic keratins | | Luster | Smoothness | Texture |
| Products of the present invention | The one obtained in Example 1 | o | o | o |
| | The one obtained in Example 2 | o | o | o |
| Comparative products | Oxidation decomposition products of wool in an alkaline solvent (Molecular weight: 50,000) | Δ | Δ | Δ |
| Control | Alkali hydrolyzed products of collagen (Molecular weight: 2,000) | Δ | Δ | Δ |
| | No addition | X | X | X |

(In the Table, the symbols in the evaluated items represent evaluations as follows: o for "excellent", Δ for "good", and X for "inferior".)

EXAMPLE 20: HAIR LIQUID

| Composition: | | |
|---|---|---|
| (A) | Cationic keratin (the one obtained in Example 3) | 1.0% |
| (B) | Polyoxypropylene (30) butyl ether | 15.0% |
| (C) | Ethanol | 40.0% |
| (D) | Water | 44.0% |

Method for the preparation:

The above components A to D were mixed and completely dissolved one another, whereby a hair liquid was obtained.

EXAMPLE 21: HAIR TONIC

| Composition: | | |
|---|---|---|
| (A) | Cationic keratin (the one obtained in Example 4) | 0.5% |
| (B) | Aluminum salt of pyrrolidonecarboxylic acid (PCA-Al) | 0.5% |
| (C) | Ethanol | 55.0% |
| (D) | Water | 44.0% |

Method for the preparation:

The above mentioned components A to D were mixed and stirred until a homogeneous mixture is obtained. Thus, a hair tonic was obtained.

What is claimed is:

1. A cationic keratin derivative which is obtained by reacting a part or whole of functional groups of keratin with a cationizing agent which contains in its molecule a group or groups of the formula

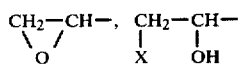

or $CH_2=CH-$ wherein X represents a halogen atom, and a quaternary nitrogen atom.

2. A cationic keratin derivative according to claim 1, wherein the part or whole of functional groups of keratin is modified with a cationic group of the following formula

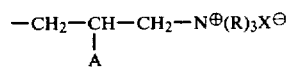

wherein each R represents a lower alkyl group or an aryl group, X represents a halogen atom, and A represents a hydrogen atom or a hydroxyl group.

3. A cationic keratin derivative according to claim 2, wherein said cationic group is β-hydroxy-γ-trimethylammoniopropyl group or γ-trimethylammoniopropyl group.

4. A process for preparing cationic keratin derivative which comprises the steps of treating a keratin material or its hydrolyzed product with a reducing agent in water or in a mixture of water and a hydrophilic organic solvent to convert difulfide bonds in the keratin material into sulfhydryl groups, and reacting a ationizing agent containing in its molecule both a group or groups of the following formulas

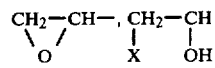

and $CH_2=CH-$ wherein X is a halogen atom, and a quaternary nitrogen atom.

5. A process according to claim 4, wherein the amount of said reducing agent is in the range of from 2 to 10 times in equivalent of disulfide bonds of the keratin material and the pH of the reaction system is in the range of from 2 to 12.

6. A process according to claim 4, wherein the amount of the cationizing agent is in the range of 0.1 to 6 times in equivalent of sulfhydryl groups present in the reduction decomposition product.

7. A hair treating cosmetic composition comprising the derivative of claim 1.

8. A hair treating cosmetic composition according to claim 7, wherein the amount of the derivative is from 0.01 to 10% by weight of the composition.

* * * * *